United States Patent [19]

Steffen et al.

[11] Patent Number: 4,584,299

[45] Date of Patent: Apr. 22, 1986

[54] METHOD OF TREATING HEART FAILURE AND MEDICAMENTS THEREFOR

[75] Inventors: Robert P. Steffen; Dale B. Evans, both of Saline; Harvey R. Kaplan; Jerry A. Weisbach, both of Ann Arbor, all of Mich.

[73] Assignee: Warner-Lambert Company, Morris Plains, N.J.

[21] Appl. No.: 612,275

[22] Filed: May 21, 1984

[51] Int. Cl.$^4$ .................. A61K 31/50; A61K 31/495
[52] U.S. Cl. .................................................. 514/252
[58] Field of Search ............... 424/250, 258; 514/252

[56] References Cited

U.S. PATENT DOCUMENTS

| | | | |
|---|---|---|---|
| 4,004,012 | 1/1977 | Lesher et al. | 424/263 |
| 4,217,347 | 8/1980 | Horovitz et al. | 424/246 |
| 4,313,951 | 2/1982 | Lesher et al. | 424/263 |
| 4,344,949 | 8/1982 | Hoefle et al. | 424/258 |
| 4,353,905 | 10/1982 | Sircar et al. | 424/250 |
| 4,425,355 | 1/1984 | Hoefle et al. | 424/274 |

FOREIGN PATENT DOCUMENTS

| | | |
|---|---|---|
| 0049605 | 4/1982 | European Pat. Off. . |
| 0061186 | 9/1982 | European Pat. Off. . |
| 0065301 | 11/1982 | European Pat. Off. . |
| 0075436 | 3/1983 | European Pat. Off. . |

OTHER PUBLICATIONS

Chem. Abst. 98, 107792k (1983)—Wu.
Chem. Abst. 98, 216005(b)(1983)—Tanabe Seiyaku.
Chem. Abst. 100, 51595(p)(1984)—Hilbull et al.
Chem. Abst. 101, 387(k)(1984)—Kaplan et al.

Primary Examiner—Douglas W. Robinson
Attorney, Agent, or Firm—Joan Thierstein

[57] ABSTRACT

Method for treating heart failure by increasing myocardial contractility and cardiac output with the administration of a pharmaceutical composition containing a combination of active ingredients including a pyridazinone or pyridin-one cardiotonic agent and a tetrahydroisoquinoline-3-carboxylic or octahydro-1H-indole-2-carboxylic acid ACE inhibitor.

7 Claims, No Drawings

METHOD OF TREATING HEART FAILURE AND MEDICAMENTS THEREFOR

BACKGROUND OF THE INVENTION

Cardiotonic agents such as 4,5-dihydro-6-(substituted)-phenyl-3(2H)-pyridazinone are described in U.S. Pat. No. 4,353,905. Cardiotonic agents such as 1,2-dihydro-5-(substituted)-phenyl]-2-oxo-3-pyridinecarbonitriles are described in U.S. application Ser. No. 515,799 of July 22, 1983. Other cardiotonic agents have been reported in U.S. Pat. No. 4,004,012 and 4,313,951.

Antihypertensive agents which attribute their activity to inhibition of angiotensin-converting enzyme (ACE inhibitors) have been described. For example, aryl derivatives of 1,2,3,4-tetrahydro-isoquinoline-3-carboxylic acids are described in U.S. Pat. No. 4,344,949 and acylated octahydro-1H-indole-2-carboxylic acids are described in U.S. Pat. No. 4,425,355.

Combinations of antihypertensive agents and diuretics are well-known in the art. ACE-inhibiting antihypertensive agents have also been reported to be useful in combination with diuretic compounds in U.S. Pat. No. 4,217,347. Combinations of ACE inhibitors with diuretics, saluretics, α-adrenolytics, β-blockers, calcium antagonists or vascular dopaminergic receptor agonists are reported in European Patent Publications 51,020, 69,846, and 49,658.

The present invention relates to a combination of certain ACE-inhibitors with certain cardiotonic agents resulting in a synergistic increase in myocardial contractility and cardiac output thereby rendering such combinations useful in treating heart failure.

SUMMARY OF THE INVENTION

Accordingly the present invention relates to a pharmaceutical composition for increasing cardiac contractility and cardiac output comprising:

(a) an effective amount of a compound of the formula

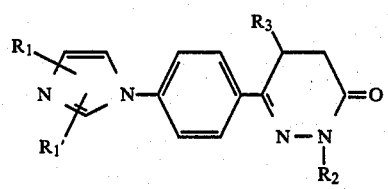

wherein $R_1$ and $R'_1$ are independently hydrogen or alkyl of one to three carbon atoms; $R_2$ is hydrogen, alkyl of one to three carbon atoms or 2-hydroxyethyl, and $R_3$ is hydrogen or alkyl of one to three carbon atoms, or a pharmaceutically acceptable acid addition salt thereof, or an effective amount of a compound of the formula

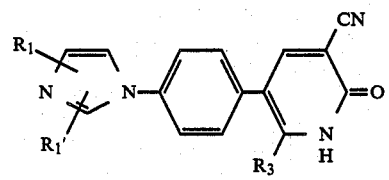

wherein $R_1$, $R'_1$, and $R_3$ are as defined above, or a pharmaceutically acceptable acid addition salt thereof, with (b) an effective amount of a compound of the formula

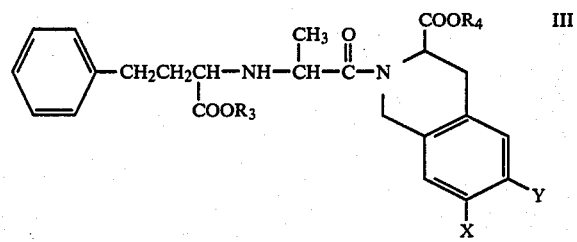

wherein $R_3$ is as defined above; $R_4$ is hydrogen or alkyl of one to three carbon atoms; X and Y are hydrogen or methoxy, or a pharmaceutically acceptable basic salt thereof, or an effective amount of 1-[2-[(1-carboxy-3-phenylpropyl)amino]-1-oxopropyl]-octahydro-1H-indole-2-carboxylic acid, its mono- or dialkylester of one to three carbon atoms, or a pharmaceutically acceptable basic salt thereof, and a pharmaceutically acceptable carrier.

The present invention also relates to a method of treating heart failure in a subject suffering therefrom comprising administering to said subject a combination of (a) an effective amount of a compound of the formula I or II with (b) an effective amount of a compound of the formula III or 1-[2-[(1-carboxy-3-phenylpropyl)amino]-1-oxopropyl]-octahydro-1H-indole-2-carboxylic acid, its mono- or dialkylester of one to three carbon atoms, or a corresponding pharmaceutically acceptable acid addition or basic salt thereof, and a pharmaceutically acceptable carrier.

DETAILED DESCRIPTION

The compounds of formulae I and II have been reported as cardiotonic agents and their effectiveness demonstrated in standard pharmacological test procedures, for example, in causing a significant increase in the myocardial contractility in the pentobarbital anesthetized dog with low or minimal changes in heart rate and blood pressure, see U.S. Pat. No. 4,353,905 and U.S. application Ser. No. 515,799 of July 22, 1983.

The compounds of formula III and the octahydro-1H-indoles defined above have been reported to be angiotensin converting enzyme inhibitors which intervene in the angiotensinogen →renin →angiotensin I →angiotensin II mechanism and are effective in reducing or alleviating hypertension, see U.S. Pat. Nos. 4,344,949 and 4,425,355, respectively.

This invention relates to the discovery that the combination of a cardiotonic agent as defined above with an ACE inhibitor as defined above results in a synergistic increase in myocardial contractility and cardiac output and therefore may be used in pharmaceutical compositions for treating heart failure.

Preferred combinations are those containing
(a) a compound of formula I wherein $R_1$, $R'_1$ and $R_2$ are hydrogen, and $R_3$ is hydrogen or methyl, with
(b) a compound of formula III, wherein $R_3$ is hydrogen or alkyl of one to three carbon atoms; $R_4$ is hydrogen, and X and Y are hydrogen or methoxy; 1-[2-[(1-carboxy-3-phenylpropyl)amino]-1-oxopropyl]-octahydro-1H-indole-2-carboxylic acid, or 1-[2-[(1-carboethoxy-3-phenylpropyl)amino]-1-oxopropyl]-octahydro-1H-indole-2-carboxylic acid.

More preferred combinations are those containing (a) a compound of formula I wherein $R_1$, $R'_1$, and $R_2$ are hydrogen and $R_3$ is hydrogen or methyl, with (b) 2-[2-[(1-carboxy-3-phenylpropyl)amino]-1-oxopropyl]-1,2,3,4-tetrahydroisoquinoline-3carboxylic acid or 2-[2-[(1-carboethoxy-3-phenylpropyl)amino]-1-oxopropyl]-1,2,3,4-tetrahydroisoquinoline-3-carboxylic acid.

Particular preferred combinations in pharmaceutical composition form are those containing 4,5-dihydro-6-[4-(1H-imidazol-1-yl)phenyl]-3(2H)-pyridazinone as the cardiotonic agent and either 2-[2-[(1-carboxy-3-phenylpropyl)amino]-1-oxopropyl]-1,2,3,4-tetrahydroisoquinoline-3-carboxylic acid or 2-[2-[(1-carboethoxy-3-phenylpropyl)amino]-1-oxopropyl]-1,2,3,4-tetrahydroisoquinoline-3-carboxylic acid.

The ACE inhibitor components in the combination have asymmetric carbon atoms. The compounds accordingly exist as optical isomers and diastereomers or as racemates and mixtures thereof. All of these are within the scope of the invention. The 1,2,3,4-tetrahydroisoquinoline-3-carboxylic acid used in this invention has the L configuration. This configuration has been shown to be required for biological activity, and thus ACE inhibitors of the invention are derived from either L(—) or DL-1,2,3,4-tetrahydroisoquinoline-3-carboxylic acid.

Single crystal x-ray diffraction analysis of the N-3-bromobenzoyl derivative of octahydro-1H-indole-2-carboxylic acid used as a starting material in this invention has shown that the cyclohexane and pyrrole ring junction is the cis configuration, with the carboxylic acid group of the pyrrole ring disposed cis to the fused cyclohexane ring, i.e.,

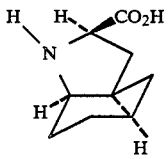

Furthermore, octahydro-1H-indole-2-carboxylic acid has been resolved via the α-phenylethylamine salt of its N-benzoyl derivative. Biologically active compounds are derived from either the racemic or levorotatory forms of octahydro-1H-indole-2-carboxylic acid. The S configuration at the asymmetric centers is preferred.

The cardiotonic compounds of formula I and II can be produced as described in U.S. Pat. No. 4,353,905 and U.S. application Ser. No. 515,799 of July 22, 1983, respectively.

The antihypertensive ACE inhibitors can be produced as described in U.S. Pat. No. 4,344,949 for the isoquinoline-3-carboxylic acids and in U.S. Pat. No. 4,425,355 for the octahydro-indole-2-carboxylic acids. According to this invention, a combination of a cardiotonic compound and an ACE inhibitor is administered in an effective amount which comprises a total daily dosage of about 1 to 200 mg, preferably 1 to 20 mg of cardiotonic agent and about 1 to 100 mg, preferably 1 to 20 mg of the ACE inhibitor to a subject, e.g., a mammalian species, suffering from heart failure. Such total daily dosages can be used in a single administration of the total amount or in divided doses two to four times daily. Generally, once or twice daily is preferred. This preferred dosage is about 3 to 60 mg of cardiotonic agent and about 3 to 60 mg of the ACE inhibitor once daily or about 1 to 20 mg of cardiotonic and about 1 to 20 mg of ACE inhibitor twice daily. The preferred route of administration is oral.

The pharmaceutical compositions of the invention can take any of a wide variety or oral and parenteral dosage forms. The dosage forms comprise as the active components, a cardiotonic compound as defined previously and an ACE inhibitor as defined previously as free bases and free acids thereof or as corresponding pharmaceutically acceptable salts.

For preparing pharmaceutical compositions, one uses inert, pharmaceutically acceptable carriers that can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compounds. In the tablet, the active compounds are mixed with carrier having the necessary binding properties in suitable proportions and compacted in the shape and size desired. The powders and tablets preferably contain from 5% or 10% to about 70% of active ingredients. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compounds with encapsulating material as carrier, providing a capsule in which the active components (with or without other carriers) are surrounded by carrier, which are thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active components in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of active components. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compounds in a unit dose of preparation may be varied or adjusted from 1 mg to 200 mg according to the particular application and the potency of the active ingredients.

In therapeutic use as a cardiotonic agent, the compositions are constituted such that the active ingredients content can be conveniently at the initial oral dosage of about 0.03 mg to about 10 mg per kilogram of weight. An active ingredients content such as to give a dose range of about 0.1 mg to about 3 mg of active ingredients per kilogram is preferred.

The pharmaceutical compositions preferably are constituted so that they can be administered parenterally or orally. Solutions of the active compounds as free bases and free acids or pharmaceutically acceptable salts can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients, into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of active ingredients plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active materials calculated to produce the desired therapeutic effect in association with the required pharmaceutical carrier. The specification for the novel dosage unit forms of the invention are dictated by and directly dependent on (a) the unique characteristics of the active materials and the particular therapeutic effect to be achieved, and (b) the limitation inherent in the art of compounding such active materials for the treatment of disease in living subjects having a diseased condition in which bodily health is impaired as herein disclosed in detail.

The principal active ingredients are compounded for convenient and effective administration in effective amounts with a suitable pharmaceutically-acceptable carrier in dosage unit form as hereinbefore disclosed. A unit parenteral dosage from can, for example, contain the principal active compounds in amounts ranging from about 0.03 to about 100 mg, with from about 0.1 to 50 mg being preferred. Expressed in proportions, the active compounds are generally present in from about 0.03 to about 100 mg/ml of carrier. The daily parenteral doses for mammalian subjects to be treated ranges from 0.03 mg/kg to 30 mg/kg. The preferred daily dosage range is 0.1 mg/kg to 3.1 mg/kg.

The active substances described above form commonly known, pharmaceutically acceptable salts such as alkali metal and other common basic salts or acid addition salts, etc. References to the base substances are therefore intended to include those common salts known to be substantially equivalent to the parent compound and described in the above referenced patents.

The following nonlimiting examples illustrate the inventors' preferred methods for preparing the compounds of the invention.

EXAMPLE 1

4,5-Dihydro-6-[4-(1H-imidazol-1-yl)phenyl]-5-methyl-3(2H)-pyridazinone

A suspension of KCN (6.6g in 8 ml of water) is added slowly to a stirred solution of a mixture of 1-[4-(1H-imidazol-1-yl)phenyl]carboxaldehyde [17.2 g, prepared by following the procedure of L. M. Sitkina and A. M. Simonov, *Khim Geterotsikl. Soedin. Akad. Nauk. Latv. SSR*, 1,143 (1966)—*Chem. Abstr.* 65, 13686 (1966)]p-toluenesulfonic acid (19 g) and morpholine (11.4 g) in dioxane (100 ml). The mixture is refluxed for three hours, concentrated to half its volume and poured into saturated $K_2CO_3$ solution. The oil is extracted with $CH_2Cl_2$, the $CH_2Cl_2$ extract is washed with water, dried, and evaporated to yield an oil which is filtered through silica gel. The oil is finally crystallized from ether to give 16.1 g of the desired morpholineacetonitrile adduct, mp. 138°–139° C.

To a stirred solution of the above morpholineacetonitrile [4-(1H-imidazol-1-yl)phenyl]-4-morpholineacetonitrile (14 g) in THF (120 ml) is added 30 drops of 30% KOH in methanol followed by a slow addition of crotononitrile (4.2 g) over a period of 15 minutes. The resulting reaction mixture is stirred at room temperature for 90 minutes, the reaction mixture is concentrated in vacuo, and the residue is treated with water and the oil is extracted with $CH_2CL_2$. The extract is washed with water, dried, and concentrated. The resulting viscous gum is dissolved in 30 ml of 6N HCl, heated on a steam bath for six hours, and the reddish solution is evaporated to dryness in vacuo. The residue is dissolved in water and pH is adjusted to 8.0. The gummy material is removed by extraction with $CH_2Cl_2$ and the aqueous solution is acidified to pH 5.0. The crystalline material is filtered, washed with water, and finally crystallized from 2-propanol to give 10.4 g of 4-(1$\underline{H}$-imidazol-1-yl)-β-methyl-γ-oxobenzenebutanoic acid, mp 181°–182° C.

An ethanolic solution (60 ml) of the above acid (10.4 g) containing 85% hydrazine hydrate (2.5 ml) is heated under reflux for four hours. The solution is cooled, diluted with water, and filtered. The solid is crystallized from ethanol/tetrahydrofuran to yield 7.6 g of the product, 4,5-dihydro-6-[4-(1$\underline{H}$-imidazol-1-yl)phenyl]5-methyl-3(2$\underline{H}$)-pyridazinone, mp 197°–198° C.

Anal calcd for $C_{24}H_{24}N_4O$: C, 66.12; H, 5.55; N, 22.04.

Found: C, 66.12; H, 5.54; N, 21.95.

Hydrochloric acid-addition salt of 4,5-dihydro-6-[4-(1$\underline{H}$-imidazol-1-yl)phenyl]-5-methyl-3(2$\underline{H}$)-pyridazinone is prepared by adding an ethanolic solution of hydrochloric acid to a hot solution of 70 g of 4,5-dihydro-6-[4-(1$\underline{H}$-imidazol-1-yl)phenyl]-5-methyl-3(2$\underline{H}$)pyridazinone in about 1400 ml of ethanol to a pH of about 2.0, chilling the mixture and collecting the precipitated salt, 78 g, mp 296°–298° d.

Anal calcd for $C_{14}H_{14}N_4O$, HCl: C, 57.83; H, 5.20; N, 19.27;

Found: C, 57.99; H, 5.07; N, 19.30.

EXAMPLE 2

1,2-Dihydro-5-[4-(1$\underline{H}$-imidazol-1-yl)phenyl]-6-methyl-2-oxo-3-pyridinecarbonitrile—Procedure A A mixture of 1,2-dihydro-5-(4-fluorophenyl)-6-methyl-2-oxo-3-pyridinecarbonitrile (5.0 grams), imidazole (25 grams), potassium carbonate (5 grams), copper (0.5 grams) and copper (I) iodide (0.5 grams) is heated just at 200° C. for 24 hours and then at 260° C. for eight hours. After cooling, the reaction mixture is diluted with water and filtered. The filtrate is acidified with 6N hydrochloric acid and the precipitate is collected. This solid is boiled in one liter of methanol and the hot mixture is filtered. The filtrate is evaporated to a volume of 200 ml and cooled to give 0.7 grams of 1,2-dihydro-5-[4-(1$\underline{H}$-imidazol-1-yl)phenyl]-6-methyl-2-oxo-3-pyridinecarbonitrile: mp 300°–301° C.

The following representative Examples 3 through 6, are given as illustrative pharmaceutical compositions utilizing different carriers. In these examples, Example 3 illustrates the use of the combination of compounds of the invention in injectables suitable for intravenous or other types of injection into the host subject. Example 4 is directed to an oral syrup preparation, Example 5 to an oral capsule preparation, and Example 6 to oral tablets. In each of Examples 3 through 6, the ingredients are first listed and are then followed by the method of preparing the composition.

EXAMPLE 3

INJECTABLES 4,5-Dihydro-6-[4-(1$\underline{H}$-imidazol-1-yl)phenyl]-3(2$\underline{H}$)-pyridazinone (A) 10 mg–200 mg 2-[2-[(1-carboxy-3-phenylpropyl)amino]-1-oxopropyl]-1,2,3,4-tetrahydroisoquinoline-3-carboxylic acid (B) 10 mg–200 mg Water for Injection USP q.s.

The hydrochloride salt of product (A) and product (B) are dissolved in the water and passed through a 0.22 micron filter. Aliquots of the filtered solution is added to ampoules or vials, sealed and sterilized.

EXAMPLE 4

| SYRUP 200 mg Active ingredients/5 ml syrup | |
|---|---|
| COMPOUND A (EXAMPLE 3) | 12.5 g |
| 2-[2-[(1-carboethoxy-3-phenylpropyl)amino]-1-oxo-propyl]-1,2,3,4-tetrahydroisoquinoline-3-carboxylic acid (C) | 12.5 g |
| Purified Water USP | 200 ml |
| Cherry Syrup q.s. or | 1000 ml |

COMPOUNDS A and C are dissolved in the water and to this solution the syrup is added with mild stirring.

EXAMPLE 5

| CAPSULES 50 mg, 100 mg or 200 mg | |
|---|---|
| COMPOUND A (EXAMPLE 3) | 250 g |
| COMPOUND C (EXAMPLE 4) | g |
| Lactose USP, Anhydrous q.s. or | 250 g |
| Sterotex Powder HM | 5 g |

Combine COMPOUNDS A, C, and the Lactose in a Tumble blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. Appropriate sized capsules are filled with 141 mg. 352.5 mg or 705 mg of the blend, respectively, for the 50 mg, 125 mg, and 250 mg containing capsules.

EXAMPLE 6

| TABLETS 50 mg, 100 mg or 200 mg | |
|---|---|
| COMPOUND A (EXAMPLE 3) | 125 g |
| COMPOUND C (EXAMPLE 4) | 125 g |
| Corn Starch NF | 200.0 g |
| Cellulose, Microcrystalline | 46.0 g |
| Sterotex Powder HM | 4.0 g |
| Purified Water q.s. or | 300.0 ml |

Combine the corn starch, the cellulose and Compounds A and C, together in a planetary mixer and mix for two minutes. Add the water to this combination and mix for one minute. The resulting mix is spread on trays and dried in a hot air oven at 50° C. until a moisture level of 1 to 2 percent is obtained. The dried mix is then milled with a Fitzmill through a #RH2B screen, and added back to the milled mixture and the total blended for five minutes by drum rolling. Compressed tablets of 150 mg, 375 mg, and 750 mg respectively, of the total mix are formed with appropriate sized punches for the 50 mg, 125 mg, or 500 mg containing tablets.

The usefulness of the pharmaceutical compositions of the present invention as cardiotonic preparations is demonstrated by the synergy of the combined active components contained therein in standard pharmacological test procedures. The following is illustrative: I.

Angiotensin Converting Enzyme Inhibition by 2-[2-[(1-carboxy-3-phenylpropyl)amino]-1-oxopropyl]-1,2,3,4-tetrahydroisoquinoline-3-carboxylic acid (B) in the Anesthetized Dog

Methods

Barbiturate anesthetized, vagotomized dogs were mechanically respired with room air. Arterial blood pressure and heart rate were recorded continuously. A series of autonomic drug challenges including angiotensin I and angiotensin II, each of which produced characteristic and reproducible blood pressure and heart rate responses, was administered before and after rising intravenous doses of 0.03, 0.3, and 3.0 mg/kg of B.

Results

Compound B had no effect on blood pressure or heart rate at the doses tested. Compound B selectively inhibited the vasopressor response to angiotensin I while having no significant effect on angiotensin II (Table 1).

TABLE 1

Effects of 2-[2-[(1-carboxy-3-phenylpropyl)-amino]-1-oxopropyl]-1,2,3,4-tetrahydro-isoquinoline-3-carboxylic acid (B) on Angiotensin I and Angiotensin II Pressor Response in Anesthetized Dogs (N = 2)

| B, mg/kg IV | Mean Blood Pressure Change (mm Hg) | |
|---|---|---|
| | Angiotensin I | Angiotensin II |
| Control[a] | 51 ± 14 | 53 ± 15 |
| .03 | 43 ± 21 | 58 ± 16 |
| .30 | 8 ± 3 | 66 ± 14 |
| 3.0 | 0 ± 0 | 72 ± 14 |

[a]Control mean blood pressure was 135 ± 8 mm Hg

The results of these studies demonstrate that B, 0.3 mg/kg or greater, effectively inhibits angiotensin converting enzyme as reflected by inhibition of angiotensin I's but not angiotensin II's vasopressor response.

II. Synergistic Hemodynamic Effects of the Angiotensin Converting Enzyme Inhibitor B and the Cardiotonic 4,5-dihydro-6-[4-(1H)-imidazol-1-yl)-phenyl]-3(2H)-pyridazinone (A) in Acute Heart Failure in the Anesthetized Dog.

Methods

Adult mongrel dogs of either sex were anesthetized with sodium pentobarbital and ventilated artificially with a positive pressure respirator. Anesthesia was maintained by a continuous infusion of pentobarbital. Arterial blood pressure, left intraventricular pressure, and its first derivative dP/dt (an index of myocardial contractility), and heart rate were recorded continuously. Cardiac output, measured by thermodilution, was recorded before myocardial depression, when stable myocardial depression was achieved (approximately 30 minutes), and ten minutes following each dosage. Following surgical preparation animals were allowed 30 minutes to stabilize hemodynamically prior to induction of myocardial depression. Myocardial depression was induced and maintained by administration of dl-propranolol at 4 mg/kg IV bolus and continuous infusion of 0.125 mg/kg/min. Once stable depression was achieved, animals received either (a) B at 0.3 mg/kg followed by A in rising doses from 0.01 to 1.0 mg/kg, n=6, (b) saline followed by A 0.01 to 1.0 mg/kg, n=6. Each agent was given as an IV bolus. Cardiodynamic and hemodynamic measurements were taken prior to, following stable myocardial depression, and ten minutes following each bolus injection. Ten minutes were sufficient to achieve stable response to each dose.

A paired t-test was used to compare intragroup data following propranolol depression.

Results

Compound A in the presence of Compound B produced greater increases in myocardial contractility (dP/dt max of left ventricular pressure) and cardiac output than A alone at comparable doses (Table 2).

TABLE 2

Effects of Compound A versus A in the Presence of Compound B on Myocardial Contractility and Cardiac Output on Propranolol-Induced Myocardial Depression in the Anesthetized Dog

| A mg/kg IV | Change from Control[a] (Mean ± SEM) | | | |
|---|---|---|---|---|
| | A (N = 6) | | B[b] + A (N = 6) | |
| | dP/dt max mm Hg sec | cardiac output ml/min | dP/dt max mm Hg sec | cardiac output ml/min |
| Control[c] | 791 ± 109 | 960 ± 100 | 921 ± 135 | 1260 ± 130 |
| 0.0 | −43 ± 26 | 10 ± 20 | 45 ± 22 | 70 ± 50 |
| 0.0 | −10 ± 55 | 50 ± 50 | 146 ± 41* | 240 ± 90* |
| 0.1 | 106 ± 67 | 200 ± 110 | 400 ± 85* | 530 ± 100* |
| 0.3 | 365 ± 54* | 580 ± 220* | 639 ± 117* | 570 ± 140* |
| 1.0 | 474 ± 92* | 640 ± 230* | 756 ± 164* | 650 ± 130* |

[a]Change from pre-A values.
[b]B, 0.3 mg/kg IV administered ten minutes before A.
[c]Control levels of dP/dt max and cardiac output preceding administration of A.
*p < 0.05 from control.

In view of the observation that Compound B per se did not increase either myocardial contractility or cardiac output, the results of these studies indicates a synergistic and beneficial effect of the combination of 2-[2-[(1-carboxy-3-phenylpropyl)-amino]-1-oxopropyl]-1,2,3,4-tetrahydroisoquinoline -3-carboxylic acid (B) and 4,5-dihydro-6[4-(1H-imidazol-1-yl) phenyl]-3(2H)-pyridazinone (A) in a model of heart failure.

We claim:

1. A pharmaceutical composition for increasing myocardial contractility and cardiac output comprising
(a) 1–200 mg of a compound of the formula

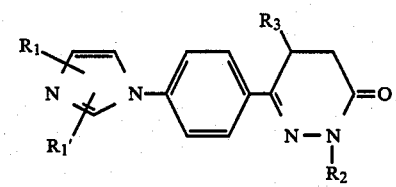

wherein $R_1$ and $R_1^1$ are independently hydrogen or alkyl of one to three carbon atoms; $R_2$ is hydrogen, alkyl of one to three carbon atoms or 2-hydroxyethyl, and $R_3$ is hydrogen or alkyl of one to three carbon atoms, or a pharmaceutically acceptable acid addition salt thereof, (b) 1–100 mg of a compound of the formula

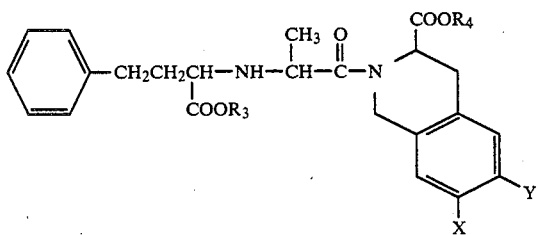

wherein R₃ is as defined above; R₄ is hydrogen or alkyl of one to three carbon atoms; X and Y are hydrogen or methoxy, or pharmaceutically acceptable basic salt thereof, in admixture with a pharmaceutically acceptable carrier.

2. A composition as claimed in claim 1, wherein in (a), R₁, R′₁ and R₂ are hydrogen, and R₃ is hydrogen or methyl.

3. A composition as claimed in claim 2, wherein in (b), R₃ is hydrogen or alkyl of one to three carbon atoms; R₄ is hydrogen, and X and Y are hydrogen or methoxy.

4. A composition as claimed in claim 2, wherein in (b), the component being 2-[2-[(1-carboxy-3-phenylpropyl)amino]-1-oxopropyl]-1,2,3,4-tetrahydroisoquinoline-3-carboxylic acid or 2-[2-[(1-carboethoxy-3phenylpropyl) amino]-1-oxopropyl]-1,2,3,4-tetrahydroisoquinoline-3-carboxylic acid.

5. A composition as claimed in claim 4, containing (a) 4,5-dihydro-6-[4-(1H-imidazol-1-yl)phenyl]-3(2H)-pyridazinone and (b) 2-[2-[(1-carboxy-3-phenyl-propyl)amino]-1-oxopropyl]-1,2,3,4-tetra-hydroisoquinoline-3-carboxylic acid.

6. A composition as claimed in claim 4, containing (a) 4,5-dihydro-6-[4-(1H-imidazol-1-yl)phenyl]-3(2H)-pyridazinone and (b) 2-[2-[(1-carboethoxy-3-phenylpropyl)amino]-1-oxopropyl]-1,2,3,4-tetrahydroisoquinoline-3-carboxylic acid.

7. A method for increasing myocardial conractility and cardiac output in a subject suffering from heart failure comprising administering either orally or parenterally to said subject a therapeutically effective amount a pharmaceutical composition as claimed in claim 1 in unit dosage form.

* * * * *